(12) United States Patent
Moskowitz

(10) Patent No.: US 6,939,534 B2
(45) Date of Patent: Sep. 6, 2005

(54) METHOD TO TREAT PULMONARY HYPOPLASIA IN THE NEWBORN

(75) Inventor: David W. Moskowitz, St. Louis, MO (US)

(73) Assignee: GenoMed, LLC, St. Louis, MO (US)

( * ) Notice: Subject to any disclaimer, the term of this patent is extended or adjusted under 35 U.S.C. 154(b) by 214 days.

(21) Appl. No.: 10/215,524

(22) Filed: Aug. 8, 2002

(65) Prior Publication Data

US 2003/0032598 A1 Feb. 13, 2003

Related U.S. Application Data

(60) Provisional application No. 60/311,663, filed on Aug. 13, 2001.

(51) Int. Cl.$^7$ .............................. A61K 9/12; A61K 9/14; A61K 9/72
(52) U.S. Cl. .............................. 424/45; 424/46; 424/43; 424/489; 514/558; 514/2
(58) Field of Search .............................. 424/45, 46, 43, 424/489; 514/558, 2

(56) References Cited

U.S. PATENT DOCUMENTS

| | | | |
|---|---|---|---|
| 4,849,350 A | 7/1989 | Yoshio et al. | |
| 4,959,353 A | 9/1990 | Brown et al. | |
| 5,230,884 A | 7/1993 | Evans et al. | |
| 5,654,007 A | 8/1997 | Johnson et al. | |
| 2002/0072540 A1 | 6/2002 | Larsson et al. | |

FOREIGN PATENT DOCUMENTS

WO    WO 97/36574    10/1997

OTHER PUBLICATIONS

Abraham et al, Importance of Angiotensin–Converting Enzyme in Pulmonary Hypertension, Cardiology 1995; 86 (suppl 1):9–15.*

Zanen, et al., "The optimal particle size for parasympathicolytic aerosols in mild asthmatics," *J. Int. J. Pharm.* 114: 111–115 (1995).

Adjei, et al., "Pulmonary delivery of peptide drugs: effect of particle size on bioavailability of leuprolide acetate in healthy mate volunteers," Pharm. Res. 7: 565–569 (1990).

Gonda, "Physico–Chemical Principles in Aerosol Delivery," in Topics in Pharmaceutical Sciences (Crommelin, et al., eds.) Medpham Scientific Publishers: Stuttgart, pp. 95–115 (1992).

Hofmann, et al., "Epidermal growth factor (EGF) concentrations in amniotic fluid and material urine during pregnancy," Acta Obstet Gynecol Scand 69(3): 217–221 (1990).

Maraschin, et al., "Toxicological evaluation of u–hEGF," Toxicol Pathol. 23: 356–366 (1995).

Miettinen, et al., "Impaired lung branching morphogenesis in the absence of functional EGF receptor," Dev Biol 186: 224–236 (1997).

Plopper, et al., "Acceleration of alveolar type II cell differentation in fetal rhesus monkey lung by administration of EGF," Am. J. Physiol 262(3.1): L313–L321(1992).

Rudt, et al., "In vitro phagocytosis assay of nano– and microparticles by chemiluminescence. I. Effect of analytical parameters, particle size and particle concentration," J. Controlled Release 22: 263–272 (1992).

Sundell, et al., "Effects of epidermal growth factor on lung maturation in fetal lambs," *Am. J. Pathol.* 100: 707–725 (1980).

Tabata, et al., "Macrophage phagocytosis of biodegradable microspheres composed of L–lactic acid/glycolic acid homo– and copolymers," *J. Biomed. Mater. Res.* 22: 837–858 (1988).

Visser, "Van der Waals and other cohesive forces affecting powder fluidization," *Powder Technology* 58: 1–10 (1989).

Yoshimura, et al., "Effect of epidermal growth factor on lung growth in experimental fetal pulmonary hypoplasia," *Early Hum Dev* 57: 61–69 (2000).

* cited by examiner

*Primary Examiner*—Gary Kunz
*Assistant Examiner*—Mina Haghighatian
(74) *Attorney, Agent, or Firm*—Sonnenschein Nath & Rosenthal LLP

(57) ABSTRACT

A method of treating pulmonary hypoplasia in infants has been developed, wherein epidermal growth factor (EGF) is administered to the pulmonary system of an infant in need of treatment thereof. The EGF is administered as an aerosol or dry powder directly to the pulmonary tree, or into the amniotic fluid before birth if a situation such as oligohydramnios is recognized pre-term. The method can also be used to treat persistent pulmonary hypertension of the newborn. A hydrophobic angiotensin I-converting enzyme (ACE) inhibitor such as ramipril can also be used for the oral treatment of persistent pulmonary hypertension of the newborn.

5 Claims, No Drawings

METHOD TO TREAT PULMONARY HYPOPLASIA IN THE NEWBORN

This application claims priority to U.S. Ser. No. 60/311,663 filed Aug. 13, 2001.

BACKGROUND OF THE INVENTION

This application is generally in the field of methods and epidermal growth factor compositions for treatment of pulmonary hypoplasia in newborn infants.

The main problem with babies born prematurely is secondary pulmonary immaturity (hypoplasia). Persistent pulmonary hypertension of the newborn (PPHN) is the result of elevated pulmonary vascular resistance to the point that venous blood is diverted to some degree through fetal channels into the systemic circulation and bypasses the lungs, resulting in systemic arterial hypoxemia.

Before birth, a developing infant depends on the fetal circulation to supply oxygen and nutrients, then eliminate $CO_2$ and other wastes via the placenta. The birth process causes dramatic changes in blood flow, bypassing the placenta, altering flow through the heart and major vessels, and opening the blood vessels within the lungs. With its first breath, an infant sets changes into motion which convert the circulatory system from that of an aquatic being to that of an air breather. As the lungs fill with air, resistance to blood flow through the lungs drops and normal blood flow begins. Two other important changes are the closure of the ductus arteriosus and of the foramen ovale. These two change the blood flow through the pulmonary artery and the heart respectively. If the changes above do not take place or only partially occur, it can create a condition known as persistent pulmonary hypertension or persistent fetal circulation.

Persistent pulmonary hypertension of the newborn is a pathophysiologic syndrome that results when the pulmonary vascular resistance fails to decrease after birth, despite improved alveolar oxygenation and lung expansion. Although systemic vascular resistance has increased (with the loss of the placenta), pulmonary vascular resistance remains equal to or greater than systemic vascular resistance. This results in blood continuing to flow through the foramen ovale and ductus arteriosus. Subsequently, with the loss of placental gas exchange and the inability to increase pulmonary blood flow, arterial oxygen tension falls to very low levels. If this situation is not reversed, the infant may die of severe hypoxemia.

Infants with persistent pulmonary hypertension are usually cyanotic with respiratory distress and tachypnea (fast respiratory rate). These infants need supplemental oxygen or, in severe cases, artificial ventilation. Diagnosis is usually confirmed by an echocardiogram which shows a large right-to-left shunting of blood through the heart and/or through a patent ductus arteriosus. Depending on severity, persistent pulmonary hypertension can quickly be fatal to a newborn. The most appropriate treatment of Persistent Pulmonary Hypertension of the Newborn remains unclear. Substantial variation in clinical practice exists between institutions. However, basic treatment goals do exist. In order of increasing aggressiveness and invasiveness: Improve alveolar oxygenation; Minimize pulmonary vasoconstriction; Maintain systemic blood pressure and perfusion; Induce an alkalotic state; Vasodilatation; Extracorporeal membrane oxygenation support. Medication, High Frequency Oscillatory Ventilation (HFOV), Inhaled Nitric Oxide (INO), and Extracorporeal Membrane Oxygenation (ECMO) are also some of the therapies used to manage these infants. HFOV is a unique type of ventilator that can increase oxygen in the blood without using high pressures that could effect pulmonary blood flow and damage the lungs themselves. INO is also delivered by a ventilator and acts as a vasodilator within the lungs opening blood vessels and reducing pulmonary blood pressures. ECMO actually acts as an artificial heart and lung, supporting blood pressure and oxygenation/ventilation.

It is readily apparent that additional, and better, treatments are needed.

It is therefore an object of the present invention to provide a treatment and compositions for treatment of pulmonary hypoplasia, and the complications associated with pulmonary hypoplasia.

SUMMARY OF THE INVENTION

A method of treating pulmonary hypoplasia in infants has been developed, wherein epidermal growth factor (EGF) is administered to the pulmonary system of an infant in need of treatment thereof. The EGF is preferably administered as an aerosol or dry powder directly to the pulmonary tree, although it can be administered into the amniotic fluid. The method can also be used to treat persistent pulmonary hypertension of the newborn.

A hydrophobic angiotensin I-converting enzyme (ACE) inhibitor such as ramipril can also be used for the oral treatment of persistent pulmonary hypertension of the newborn.

DETAILED DESCRIPTION OF THE INVENTION

I. EGF Formulations

A. EGF

In the preferred embodiment, recombinant human EGF is used to treat pulmonary hypoplasia in the newborn human. It is understood that the EGF of other species will be used to treat pulmonary hypoplasia in infants of other species. There appears to be no toxicity to EGF in animal models (e.g. no lung cancers).

U.S. Pat. No. 4,959,353 owned by the University of Louisville and Chiron Corp. describes recombinant EGF. U.S. Pat. No. 4,849,350 to Yoshio, et al., assigned to Takeda Chemical Ind. describes the production of recombinant EGF. Equivalent variants and dosage formulations can be made as described in the prior art, including chimeric proteins, and biologically active fragments.

B. Carriers

The formulations can be administered dissolved in saline or phosphate buffer, preferably formulated for aerosol delivery. Alternatively, the EGF can be administered as a powder for inhalation. In another embodiment, the EGF is formulated for injection directly into the amniotic fluid.

The term aerosol as used herein refers to any preparation of a fine mist of particles, typically less than 10 microns in diameter, which can be in solution or a suspension, whether or not it is produced using a propellant. Aerosols can be produced using standard techniques, such as ultrasonication or high pressure treatment.

Carriers can be divided into those for dry powder formulations and for administration as solutions.

1. Liquid Formulations

Aerosols for the delivery of therapeutic agents to the respiratory tract have been developed. See, for example, Adjei, A. and Garren, J. Pharm. Res., 7: 565–569 (1990); and Zanen, P. and Lamm, J.-W. J. Int. J. Pharm., 114: 111–115 (1995).

2. Dry Powder Formulations

Drug delivery by inhalation represents a well established mode of administration of low molecular weight pharmaceuticals for various lung disorders, with a promise for noninvasive systemic delivery of drugs in general. Several biopharmaceutical companies are developing methods for pulmonary delivery of peptides and proteins, with one such product already in clinical use (the enzyme DNAse produced by Genentech for the treatment of symptoms of cystic fibrosis in children). Furthermore, there is no evidence that inhaling autologous proteins presents significant immune issues.

A number of pharmaceutical preparations for pulmonary delivery of drugs has been developed. For example, U.S. Pat. No. 5,230,884 to Evans et al., discloses the use of reverse micelles for pulmonary delivery of proteins and peptides. U.S. Pat. No. 5,654,007 to Johnson et al., discloses methods for making an agglomerate composition containing a medicament powder (e.g. proteins, nucleic acids, peptides, etc.) wherein a nonaqueous solvent binding liquid (a fluorocarbon) is used to bind the fine particles into aggregated units. The agglomerate composition has a mean size ranging from 50 to 600 microns and is allegedly useful in pulmonary drug delivery by inhalation. PCT/US97/08895 by Massachusetts Institute of Technology discloses particles made of a biodegradable material or drug, which have a tap density less than 0.4 g/cm$^3$ and a mean diameter between 5 $\mu$m and 30 $\mu$m. PCT/EP97/01560 by Glaxo Group Limited discloses spherical hollow drug particulates for use in pulmonary delivery.

Dry powder formulations ("DPFs") with large particle size have improved flowability characteristics, such as less aggregation (Visser, J., Powder Technology 58: 1–10 (1989)), easier aerosolization, and potentially less phagocytosis. Rudt, S. and R. H. Muller, J. Controlled Release, 22: 263–272 (1992); Tabata, Y., and Y. Ikada, J. Biomed. Mater. Res., 22: 837–858 (1988). Dry powder aerosols for inhalation therapy are generally produced with mean diameters primarily in the range of less than 5 microns. Ganderton, D., J. Biopharmaceutical Sciences, 3:101–105 (1992); and Gonda, I. "Physico-Chemical Principles in Aerosol Delivery," in Topics in Pharmaceutical Sciences 1991, Crommelin, D. J. and K. K. Midha, Eds., Medpharm Scientific Publishers, Stuttgart, pp. 95–115, 1992, although a preferred range is between one and ten microns in aerodynamic diameter.

The formulations may further include a surfactant. Surfactants which can be used include phosphoglycerides. Exemplary phosphoglycerides include phosphatidylcholines, such as the naturally occurring lung surfactant, L-alpha.-phosphatidylcholine dipalmitoyl ("DPPC"). The use of surfactants endogenous to the lung may avoid the need for the use of non-physiologic surfactants. Other exemplary surfactants include diphosphatidyl glycerol (DPPG); 1,2-Dipalmitoyl-sn-glycero-3-phospho-L-serine (DPPS); 1,2-Dipalmitoyl-sn-glycero-3-phosphocholine (DSPC); 1,2-Distearoyl-sn-glycero-3-phosphoethanolamine (DSPE); fatty alcohols such as polyethylene glycol (PEG); polyoxyethylene-9-lauryl ether; a surface active fatty acid, such as palmitic acid or oleic acid; sorbitan trioleate (Span 85); glycocholate; surfactin; a poloxomer; a sorbitan fatty acid ester such as sorbitan trioleate; tyloxapol and a phospholipid. Surfactants which can be included in the formulation to improve their aerosolization properties include phosphoglycerides.

II. Treatment of Pulmonary Hypoplasia in Infants

Normal fetal renal development is required for normal fetal lung development, as suggested by Potter's syndrome. In this syndrome, renal agenesis is accompanied by pulmonary hypoplasia. Amniotic fluid, which is primarily derived from glomerular filtration and tubular processing by the fetal kidneys, is particularly important for pulmonary maturation. Many animal and in vitro studies have shown the promaturational effects of epidermal growth factor (EGF) on fetal lung tissue. For example, EGF applied to type II pneumocytes in culture stimulates production of surfactant, usually absent in preterm infants with secondary pulmonary hypoplasia.

EGF, derived from the thick ascending limb and distal convoluted tubule in postnatal animals, is a normal constituent of urine in all mammalian species tested. However, production of EGF by the fetal kidney has not been well studied; indeed, preliminary studies in mice suggested that EGF was not elaborated by the kidney until 1–3 days after birth.

Since the EGF receptor can be activated by either EGF or transforming growth factor-$\alpha$ (TGF-$\alpha$), and TGF-$\alpha$ is important in fetal development, and is also elaborated by the distal nephron, the EGF and TGF-$\alpha$ content of human amniotic fluid was measured, using specific radioimmunoassays and immunoprecipitation and immunoblotting. No detectable TGF-$\alpha$ (<0.6 ng/ml) and very little detectable EGF was found by direct radioimmunoassay of amniotic fluid. However, when amniotic fluid samples were acidified (pH 1–2) and then heated (100° C. for 5 min) to remove possible binding protein activity, significant amounts of EGF receptor-reactive material were observed: 6.5±1.33 ng/ml at <16 weeks gestation (mean±SEM, n=15 patients); 4.06±2.43 ng/ml at 21–25 weeks (n=7); 6.68±2.09 ng/ml at 26–30 weeks (n=14); 12.62±3.69 at 31–35 weeks (n=10); and 4.25±0.49 ng/ml at 36–40 weeks (n=10). By comparison, EGF content of neonatal urine as measured by direct radioimmunoassay was 30.1±9.0 ng/ml at day 1 (n=6) and 40.0±11.3 ng/ml at day 3 (n=5) (See also Table 1). EGF, but not TGF-$\alpha$, is stable under these conditions. Neonatal urine showed the same concentration of EGF after acidification and boiling, suggesting that it contained EGF but no binding protein activity. Immunoprecipitation and immunoblotting with antibody specific for human EGF revealed the presence of the EGF precursor (preproEGF, MW approximately 170,000 D) in amniotic fluid throughout gestation. In neonates, mature EGF (6 kD) is the predominant form in urine.

These results are summarized as follows:

No significant concentration (<0.6 ng/ml) of TGF-$\alpha$ or EGF in human amniotic fluid was detectable directly by RIA or RRA. Under conditions in which EGF but not TGF-$\alpha$ is stable (acidification to pH 1–2, heating to 100° C. for 5 min), significant EGF receptor-reactive material was present in all human amniotic fluid samples (see Table 1), suggesting the presence of EGF binding protein activity in human amniotic fluid, as well as EGF itself.

Specific immunoprecipitation and immunoblotting of all amniotic fluid samples revealed high MW EGF-immunoreactive material, consistent with the presence of the EGF precursor, preproEGF, and proteolytic cleavage products in amniotic fluid from as early as approximately 12 weeks of gestation. No mature EGF (6,000 daltons) was seen in human amniotic fluid.

The source of preproEGF in human amniotic fluid is likely to be the fetal kidney, since neonatal urine contained high concentrations of EGF-immunoreactive material (see Table 1).

Near the time of birth, two biochemical changes appear to occur: (a) a renal ectoprotease activity capable of processing preproEGF (present in amniotic fluid) to mature EGF (present in neonatal urine, data of others) appears; (b) EGF binding protein(s) disappears (Table 1).

Amniotic fluid samples were mitogenic for LLC-$PK_1$ cells in culture, a porcine proximal tubule-like cell line with surface EGF receptors. Peak mitogenic activity was present at 24–30 weeks of gestation. This suggests that the receptor- and immuno-reactive EGF which was detected in amniotic fluid is biologically active, despite the presence of EGF binding activity.

EGF has previously been shown to promote fetal lung development and maturation in vitro and in vivo [Sundell, H. W. et al. AM. J. Pathol. 100:707–725 (1980); Hofmann, G. E. and Abramowicz, J. S. Acta Obstet Gynecol Scand 69: 217–221 (1990); Plopper, C. G. et al. AM J Physiol 262(3 PART 1):L313–L321(1992); Miettinen, P. J. et al. Dev Biol 186:224–236(1997); Yoshimura, S. et al. Early Hum Dev 57:61–69(2000)]. However, this patent provides the precise doses of recombinant human EGF required at different gestational ages to result in physiologic development of the fetal lung. Under dosing can lead to insufficient pulmonary development, overdosing can lead to systemic toxicity [Marashin, R. Toxicol Pathol. 23:356–366(1995)].

The data support a mechanism whereby normal fetal renal development is required for fetal pulmonary development/ maturation. In addition, these data allow development of a schedule (beginning at less than 16 weeks of gestation) and dosage (see Table 1) for using recombinant human EGF in the prevention or treatment of pulmonary hypoplasia in humans and other mammals.

For neonates with pulmonary immaturity on mechanical ventilation, recombinant human EGF (rhEGF) can be given most easily by inhalational aerosol. The recommended concentration of rhEGF in the aerosol, depending on gestational age of the infant, is given in Table 1. These concentrations are generally applicable to all mammalian species.

For aerosolized EGF in solution, for example, a neonate delivered after only 27 weeks of gestation would receive continuous endotracheal aerosolization of a solution containing 6.5 ng/ml epidermal growth factor until it was 31 weeks old, whereupon the concentration of epidermal growth factor in the aerosol would be increased to approximately 12.5 ng/ml. After 35 weeks of gestational age, the concentration of epidermal growth factor the aerosol would be decreased to 4.5 ng/ml through week 40 of gestational age.

The dose of pulmonary surfactant currently used in the aerosol given to neonates born with pulmonary hypoplasia could be decreased accordingly.

Pre-term, intrauterine rhEGF can be administered by injection into amniotic fluid in order to stimulate pulmonary maturation of the fetus with pulmonary hypoplasia. Again, the amount of rhEGF given during gestation should result in EGF concentrations as given in Table 1.

TABLE 1

EGF Levels in Amniotic Fluid

| Weeks of Gestation | EGF (by RRA; mean ± SEM) | No. patients |
|---|---|---|
| <16 | 6.50 ± 1.33 ng/ml | n = 15 |
| 21–25 | 4.06 ± 2.43 ng/ml | n = 7 |
| 26–30 | 6.68 ± 2.09 ng/ml | n = 14 |
| 31–35 | 12.62 ± 3.69 ng/ml | n = 10 |
| 36–40 | 4.25 ± 0.49 ng/ml | n = 10 |

Abbreviations:
RRA, radioreceptor assay;
RIA, radioimmunoassay;
EGF, epidermal growth factor;
SEM, standard error of the mean.

III. Persistent Pulmonary Hypertension of the Newborn (PPHN)

Neonatal intensive care unit stays could be shortened considerably if an alternative to inhalational nitric oxide could be found. Also, the half-life of inhaled nitric oxide is very short, requiring constant treatments.

PPHN can be treated effectively with an oral hydrophobic angiotensin-I-converting enzyme inhibitor (ACE Inhibitor) such as Ramipril or Quinapril. oral ramipril is titrated upwards beginning at a dose of 1.25 mg to lower pulmonary arterial pressures. Oral Ramipril is maintained at the maximum dose for three-six months after discharge from the hospital, whereupon its use is re-evaluated. If pulmonary hypertension persists, further use of oral Ramipril is required to maintain normalized pressures of the pulmonary arteries.

Modifications and variations of the method and compositions described herein will be understood by those skilled in the art to be equivalent to and encompassed by the following claims.

I claim:

1. A method for treating or preventing pulmonary hypoplasia in a neonate in need thereof comprising:

administering recombinant human epidermal growth factor (rhEGF) to the neonate, comprising delivering to the neonate until 31 weeks of gestational age a dosage of aerosolized EGF in solution that is equivalent to continuous endotracheal aerosolization of a solution containing approximately 6.5 ng/ml rhEGF;

when the neonate is 31 weeks of gestational age, increasing the concentration of rhEGF in solution to approximately 12.5 ng/ml; and when the neonate is 35 to 40 weeks of gestational age, decreasing the concentration of rhEGF in solution to approximately 4.5 ng/ml.

2. The method of claim 1 wherein the rhEGF is administered as an aerosol.

3. The method of claim 1 wherein the rhEGF is administered as a dry powder.

4. The method of claim 1 wherein the rhEGF is administered with a pulmonary surfactant.

5. The method of claim 1 wherein a hydrophobic angiotensin I-converting enzyme (ACE) inhibitor is also administered to the neonate.

* * * * *